US012382571B2

(12) United States Patent
Shinton et al.

(10) Patent No.: US 12,382,571 B2
(45) Date of Patent: Aug. 5, 2025

(54) RADIOTHERAPY DEVICE (71) Applicant: Elekta Limited, Crawley (GB)

(72) Inventors: Ian Shinton, Crawley (GB); Duncan Bourne, Sussex (GB); Peter Doherty, Crawley (GB); Emma Wooldridge, Crawley (GB)

(73) Assignee: Elekta Limited, Crawley (GB)

( * ) Notice: Subject to any disclaimer, the term of this patent is extended or adjusted under 35 U.S.C. 154(b) by 67 days.

(21) Appl. No.: 18/005,541

(22) PCT Filed: Jul. 15, 2021

(86) PCT No.: PCT/EP2021/069871
§ 371 (c)(1),
(2) Date: Jan. 13, 2023

(87) PCT Pub. No.: WO2022/013401
PCT Pub. Date: Jan. 20, 2022

(65) Prior Publication Data
US 2023/0262868 A1   Aug. 17, 2023

(30) Foreign Application Priority Data
Jul. 16, 2020   (GB) ...................................... 2010971

(51) Int. Cl.
*H05H 7/04*   (2006.01)
*A61N 5/10*   (2006.01)
(Continued)

(52) U.S. Cl.
CPC ............. *H05H 7/04* (2013.01); *A61N 5/1077* (2013.01); *H05H 7/06* (2013.01); *H05H 7/08* (2013.01);
(Continued)

(58) Field of Classification Search
CPC .................. A61N 5/10; A61N 5/1077; A61N 2005/1087; A61N 2005/1089; H05H 6/00;
(Continued)

(56) References Cited
U.S. PATENT DOCUMENTS 4,734,653 A * 3/1988 Jahnke .................... H05H 7/04
315/501
10,236,090 B1 * 3/2019 Areti ..................... H05H 7/001
(Continued)

FOREIGN PATENT DOCUMENTS

GB   2015821 A * 9/1979 ............ G21K 1/093
SU   1088644 A2   11/1985
(Continued)

OTHER PUBLICATIONS

"British Application No. 2010971.6, Examination Report dated Mar. 6, 2024", (Mar. 6, 2024), 4 pgs.
(Continued)

*Primary Examiner* — Raymond R Chai
(74) *Attorney, Agent, or Firm* — Schwegman Lundberg & Woessner, P.A.

(57) ABSTRACT

A particle accelerator comprises a waveguide configured to accelerate a beam of electrons along an acceleration path. A diversion channel is configured to convey a beam of electrons along a diversion path. A first magnet arrangement is configured to, at a first location, direct electrons from the acceleration path to the diversion path. A second magnet arrangement is configured to, at a second location, direct electrons from the diversion path to the acceleration path.

12 Claims, 9 Drawing Sheets

(51) Int. Cl.
  *H05H 6/00*   (2006.01)
  *H05H 7/06*   (2006.01)
  *H05H 7/08*   (2006.01)
  *H05H 7/12*   (2006.01)
  *H05H 7/16*   (2006.01)
  *H05H 9/00*   (2006.01)
(52) U.S. Cl.
  CPC ............... *H05H 7/16* (2013.01); *H05H 9/00* (2013.01); *A61N 2005/1089* (2013.01); *H05H 6/00* (2013.01); *H05H 2007/045* (2013.01); *H05H 2007/065* (2013.01); *H05H 2007/084* (2013.01); *H05H 7/12* (2013.01); *H05H 2277/11* (2013.01)
(58) Field of Classification Search
  CPC .. H05H 7/04; H05H 7/06; H05H 7/08; H05H 7/12; H05H 7/16; H05H 9/00; H05H 9/04; H05H 9/048; H05H 13/10; H05H 2007/045; H05H 2007/065; H05H 2007/084; H05H 2007/122; H05H 2277/11
  See application file for complete search history.

(56) References Cited

U.S. PATENT DOCUMENTS

| | | | |
|---|---|---|---|
| 2010/0195791 A1 | 8/2010 | Ishkhanov et al. | |
| 2013/0083880 A1* | 4/2013 | Noonan | H05H 9/00 315/505 |
| 2016/0301180 A1* | 10/2016 | Nikipelov | H01S 3/0903 |
| 2017/0076830 A1* | 3/2017 | Douglas | H05H 13/10 |
| 2021/0077830 A1* | 3/2021 | Bennett | A61B 6/037 |
| 2023/0019382 A1* | 1/2023 | Doherty | H05H 9/04 |
| 2023/0262868 A1* | 8/2023 | Shinton | A61N 5/1077 315/505 |
| 2024/0090112 A1* | 3/2024 | Agustsson | G21K 5/10 |

FOREIGN PATENT DOCUMENTS

| | | | | |
|---|---|---|---|---|
| SU | 1144606 A1 | 12/1986 | | |
| WO | 2013043833 | 3/2013 | | |
| WO | WO-2016139008 A1 * | 9/2016 | ............... | G21G 1/10 |

OTHER PUBLICATIONS

"International Application Serial No. PCT/EP2021/069871, International Search Report dated Oct. 29, 2021", (Oct. 29, 2021), 4 pgs.

"International Application Serial No. PCT/EP2021/069871, Written Opinion dated Oct. 29, 2021", (Oct. 29, 2021), 9 pgs.

"United Kingdom Application Serial No. 2010971.6, Examination Report dated Nov. 18, 2020", (Nov. 18, 2020), 7 pgs.

Behre, Christopher, et al., "First lasing of the IR upgrade FEL at Jefferson Lab", Nuclear Instruments and Methods in Physics Research Section A: Accelerators, Spectrometers, Detectors and Associated Equipment 528.1-2, (Aug. 1, 2004), 19-22.

"British Application No. 2010971.6, Examination Report dated Aug. 11, 2021", (Aug. 11, 2021), 5 pgs.

* cited by examiner

RADIOTHERAPY DEVICE

PRIORITY APPLICATIONS

This application is a U.S. National Stage Filing under 35 U.S.C. § 371 from International Application No. PCT/EP2021/069871, filed on Jul. 15, 2021, and published as WO2022/013401 on Jan. 20, 2022, which claims the benefit of priority to United Kingdom Application No. 2010971.6, filed on Jul. 16, 2020; the benefit of priority of each of which is hereby claimed herein, and which applications and publication are hereby incorporated herein by reference in their entireties.

FIELD

This disclosure relates to the field of particle accelerators, and more specifically to linear accelerators, for producing beams of electrons or other charged particles.

BACKGROUND

Radiotherapy devices are an important tool in modern cancer treatment. Radiotherapy devices are large, complex machines, with many moving parts and inter-operating mechanisms. An example of a radiation source for producing an electron beam is a linear accelerator (LINAC). Clinical LINAC devices are configured to deliver high energy radiation to a patient.

Linear accelerators (especially those for medical use) accelerate electrons, or other charged particles, to relativistic speeds along an acceleration path through a waveguide. A source of electrons, for example an electron gun, is configured to inject electrons into the waveguide. The electrons are injected by the electron gun and accelerated through the waveguide. A radiofrequency (RF) electromagnetic wave is applied to the waveguide which provides an oscillating electric field within the waveguide to accelerate the electrons. The accelerated electrons hit a target and produce X-rays.

The X-rays are for medical use, for example radiotherapy treatment. The X-rays may be aimed at cancerous cells or tumours. Radiotherapy works by using the X-rays to destroy cancerous cells in the area that's being treated by damaging the DNA.

Typically, a LINAC produces a beam of electrons (and therefore X-rays) of a single energy (for example 6 MV). Spatial limitations are imposed on the LINAC, since LINACs are fitted into a radiotherapy device that requires large premises for use. It is desirable to produce a LINAC that is as small as possible.

It is also desirable to produce a LINAC that has the capability of producing a beam of electrons with multiple different energies (for example, to produce energies of both 6 MV and 10 MV in a single machine). Multiple energies are useful for varying the length of time of exposure to radiation and for modifying individual patient treatment plans depending on the patient's needs.

The present invention seeks to provide an improved waveguide for use in radiotherapy.

SUMMARY

An invention is set out in the independent claims. Optional features are set out in the dependent claims.

BRIEF DESCRIPTION OF THE DRAWINGS

Specific embodiments are described below by way of example only and with reference to the accompanying drawings in which.

DETAILED DESCRIPTION

The present disclosure relates to a waveguide for use in a particle accelerator, for example a linear accelerator (LINAC). The linear accelerator may be suitable for use in a radiotherapy device. The radiotherapy device may be suitable for delivering a beam of radiation to a patient in order to treat a tumour.

It is desirable to be able to increase the energy produced by a linear accelerator. One method of increasing the energy produced by a standing waveguide is to increase the power delivered to the waveguide, to in turn increase the energy delivered to the electrons. However, this method is typically ineffective at increasing the output energy of the electron beam due to complications with the "buncher" component of the waveguide. The electrons are bunched together using a "buncher" which slows down some electrons to allow other electrons time to catch up. The electrons are then free to move together in so called "packets" or "bunches". Waveguides are designed with "bunchers" that are optimised to produce an electron beam with a single energy. To alter the energy of the electron beam, the input power radio frequency (RF) delivered to the conventional standing waveguide that is used to accelerate the electrons configuration must be increased so that the electrons are accelerated to faster energies. However, increasing the power of the RF delivered to a conventional standing waveguide configuration can stop the "buncher" from working altogether. "Bunchers" are designed to work at single energies to align electrons in "bunches" by applying specifically defined acceleration and deceleration to different groups of electrons. Altering the power delivered to the waveguide system will affect this carefully constructed set up and stop the "buncher" from working altogether. This means that altering the power supplied to the waveguide is an ineffective way to increase the energy of the resultant electron beam.

The present application discloses a different approach to increasing the resultant energy of the electron beam. As explained in the following disclosure, in order to produce multiple energies in a LINAC standing waveguide or travelling waveguide system, the electron beam can be recirculated. This can be done by passing an electron beam through the waveguide acceleration channel more than once. The electron beam passes through the acceleration channel a first time gaining energy, then the electron beam is redirected back through the acceleration a second time to gain further energy. The electron beam gains more energy for each circulation through the acceleration channel. This results in a LINAC standing waveguide or traveling waveguide system for which different energy electron beams can be produced depending on how many times the electrons pass through the acceleration channel. For example, an electron beam which has passed through the acceleration channel twice may have up to twice much energy as an electron beam that has only passed through the acceleration channel once.

In particular, the present application relates to a dual energy particle accelerator, and further to creating a higher energy beam generated by passing the electron beam through the acceleration channel twice. Dual energy means that two different electron beams with two separate energies can be produced by the same LINAC machine. For example, the LINAC can produce a first electron beam that has been accelerated through the acceleration channel once and a second electron beam that has been accelerated through the acceleration channel twice, where the first electron beam and second electron beam have different energies. The LINAC standing waveguide or traveling waveguide system can switch configurations to produce the first and second electron beams with different energies.

Such techniques are advantageous as they allow for an increase in the energy supplied by the beam of electrons to the patient. The disclosed techniques are used to produce electron beams with greater energy and therefore deliver a higher dose rate to patients. This in turn reduces treatment time and allows more patients to be treated within a given time period. Electron beams can be used to treat patients directly or the energy in the electron beam can be transferred to X-ray beams as explained below in the overview of the LINAC overview.

High-Level Overview of a LINAC

Figure 1:
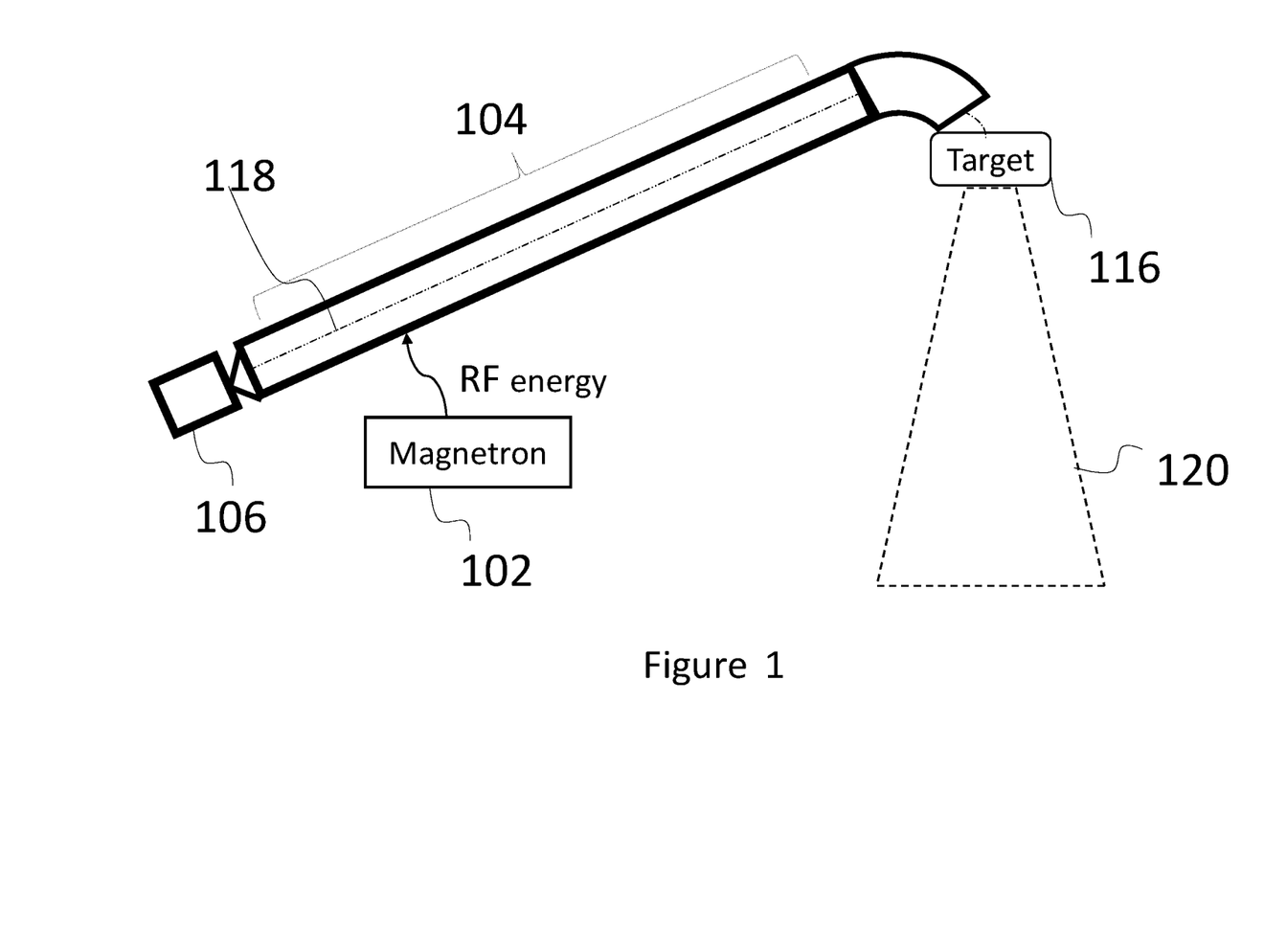
FIG. 1 illustrates a schematic illustration of a LINAC device.

FIG. 1 depicts a LINAC suitable for delivering, and configured to deliver, a beam of radiation to a patient during radiotherapy treatment. In operation, the LINAC device produces and shapes a beam of radiation and directs it toward a target region within the patient's body in accordance with a radiotherapy treatment plan.

A medical LINAC machine is by necessity complex, with many inter-operating component parts. A brief summary of the operation of a typical LINAC will be given with respect to the LINAC device depicted in FIG. 1, which comprises a source of RF waves 102, a waveguide 104, a source of electrons 106, a heavy metal target 116 which produces X-rays 120 when hit by an electron beam 118, and a treatment head which houses various apparatus configured to, for example, collimate and shape the resultant X-ray beam.

The source 102 of RF waves, such as a magnetron, produces RF waves. The source 102 of RF waves is coupled to the waveguide 104 and is configured to pulse RF waves into the waveguide 104. A source 106 of electrons, such as an electron gun, is coupled to the waveguide 104 and is configured to inject electrons into the waveguide 104. In the source 106 of electrons, electrons are thermionically emitted from a cathode filament as the filament is heated. The temperature of the filament controls the number of electrons injected. The injection of electrons into the waveguide 104 is synchronised with the pumping of the RF waves into the waveguide 104. The design and operation of the RF wave source 102, electron source 106 and the waveguide 104 is such that the RF waves accelerate the electrons to very high energies as they propagate through the waveguide 104. The design of the waveguide 104 depends on whether the LINAC accelerates the electrons using a standing wave or travelling wave, though the waveguide typically comprises a series of cells or cavities, each cell connected by a hole or 'iris' through which the electron beam 118 may pass. The acceleration cells are coupled in order that a suitable electric field pattern is produced which accelerates electrons propagating through the waveguide 104.

As the electrons are accelerated in the waveguide 104, the electron beam path 118 is controlled by a suitable arrangement of steering magnets, or steering coils, which surround the waveguide 104. The arrangement of steering magnets may comprise, for example, two sets of quadrupole magnets.

To ensure that propagation of the electrons is not impeded as the electron beam 118 travels toward the target, the waveguide 104 is evacuated using a vacuum.

When the high energy electrons hit the target, radiation is produced in a variety of directions. At this point, a collimator blocks radiation travelling in certain directions and passes only forward travelling radiation to produce a cone shaped beam. The beam can be shaped in various ways by beam-shaping apparatus, for example by using a multi-leaf collimator, before it passes into the patient as part of radiotherapy treatment.

In some implementations, the LINAC is configured to emit either an X-ray beam 120 or an electron particle beam (not shown). Such implementations allow the device to provide electron beam therapy, i.e. a type of external beam therapy where electrons, rather than X-rays, are directed toward the target region. It is possible to 'swap' between a first mode in which X-rays are emitted and a second mode in which electrons are emitted by adjusting the components of the LINAC.

The LINAC device also comprises several other components and systems. As will be understood by the person skilled in the art, a LINAC device used for radiotherapy treatment will have additional apparatus such as a gantry to support and rotate the LINAC, a patient support surface, and a controller or processor configured to control the LINAC apparatus.

Figure 2:
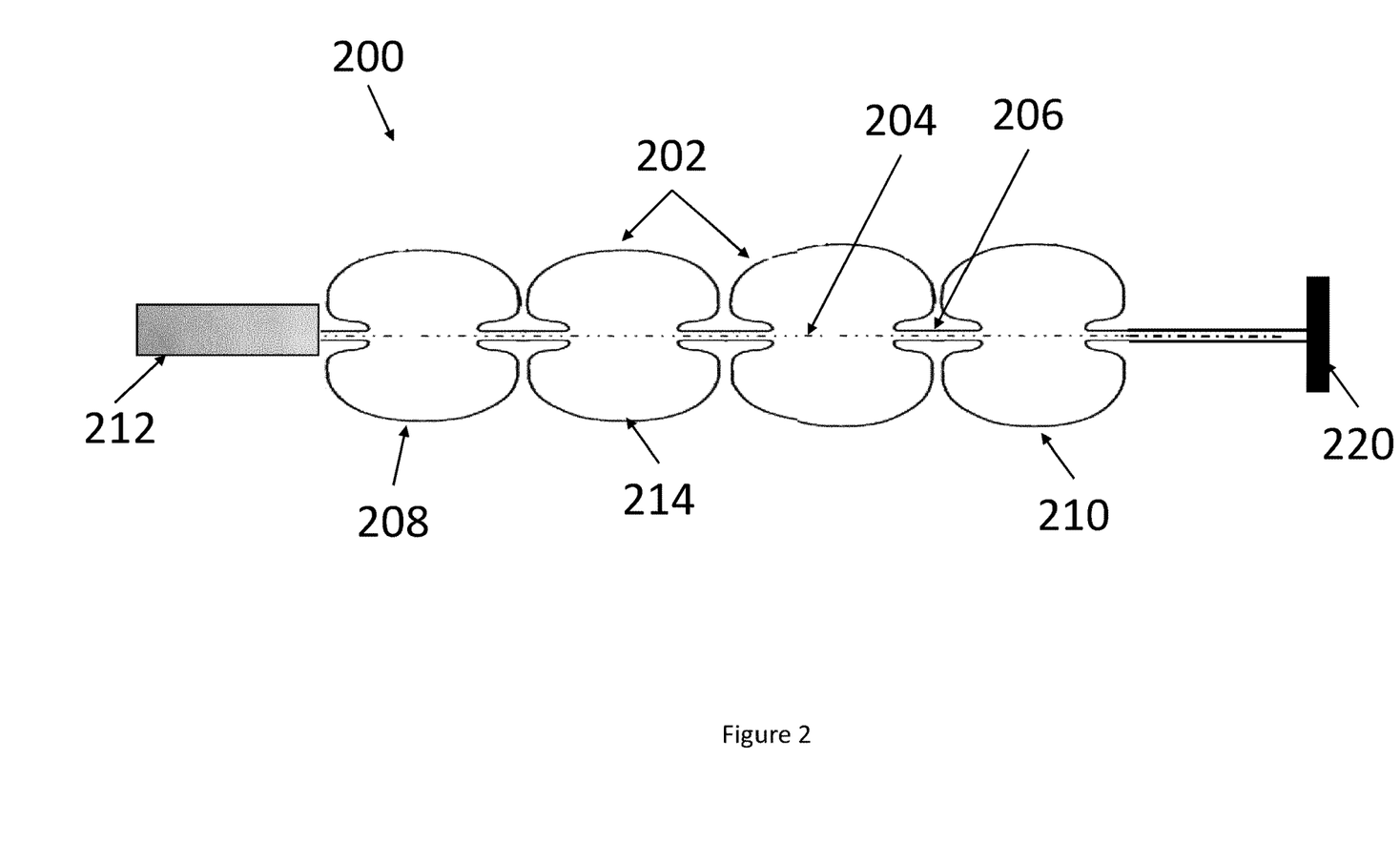
FIG. 2 illustrates a particle accelerator.

FIG. 2 illustrates a portion of a known waveguide 200. Four acceleration cells 202 of a series of connected acceleration cells are shown. The acceleration cells are each connected along a central axis 204 by irises 206. Only four acceleration cells 202 are illustrated in FIG. 2, although a typical waveguide will have more. Each cell is defined in the form of a recess within a surrounding shell of a conductive material, usually copper. The precise number will vary, dependent on the design criteria of the accelerator. A greater number of acceleration cells will typically result in a higher output energy of the waveguide. The electrons obtain extra energy for each additional acceleration cell they pass through, therefore, more acceleration cells results in a higher output energy of the resultant electron beam. To achieve a maximum energy electron beam, it is desirable to pass the electrons through as many acceleration cells as possible, however, there is a spatial limitation on the size of the LINAC in order to fit inside a standard size treatment room.

A source (not shown) of RF waves is coupled to the waveguide 200 and is configured to pulse RF waves into the waveguide 200. The design and operation of the RF wave source, electron source and the waveguide 200 is such that the RF waves accelerate the electrons to very high energies as they propagate through the waveguide 200. If a greater RF is delivered to the waveguide, the electrons receive a greater energy from the electromagnetic field produced by the RF and the output energy of the resultant electron beam will be higher. The design of the waveguide 200 depends on whether the LINAC accelerates the electrons using a standing wave or travelling wave. The acceleration cells 202 are coupled in order that a suitable electric field pattern is produced which accelerates electrons propagating through the waveguide 200. The electric field pattern accelerates electrons along an acceleration path. The acceleration path is along the central axis 204 of the acceleration cells 202 of the waveguide 200. The electron beam is 'bunched' together into pockets of electrons (i.e. the electron beam is not uniform). The electrons are bunched together using a 'buncher' which slows down some electrons to allow other electrons time to catch up. The electrons are then free to move together in packets or bunches.

Electrons enter the input accelerating cell 208 at the first end of the input accelerating cell 208. The source of electrons 212 (typically an electron gun) is located at the first end and connected to the first end of the input accelerating cell 208 to input the electrons into the input accelerating cell 208. When an electron enters the input accelerating cell 208 in the waveguide 200 it is accelerated by the RF field (i.e. electromagnetic field). The electrons traveling in the forwards direction, the forward direction being along the central axis 204 of the waveguide 100 from the first end of the input accelerating cell 208 to the target 220, gain energy and accelerate in a forward direction towards a second end of the input accelerating cell 208 and eventually into a second acceleration cell 214. The electrons travel along the waveguide 200 towards a target 220 and produce X-rays.

Recirculating Electron Beams

There is provided a dual energy (mode) particle accelerator. A dual energy particle accelerator is capable of producing two different electron beams with two separate energies. For example, an initial electron beam that has been accelerated through the acceleration channel once and a further electron beam that has been accelerated through the acceleration channel twice, where the initial electron beam and further electron beam have different energies. The LINAC standing waveguide or traveling waveguide system can switch configurations to produce the first and second electron beams with different energies depending on the requirements of the patient treatment plan.

Figure 3:
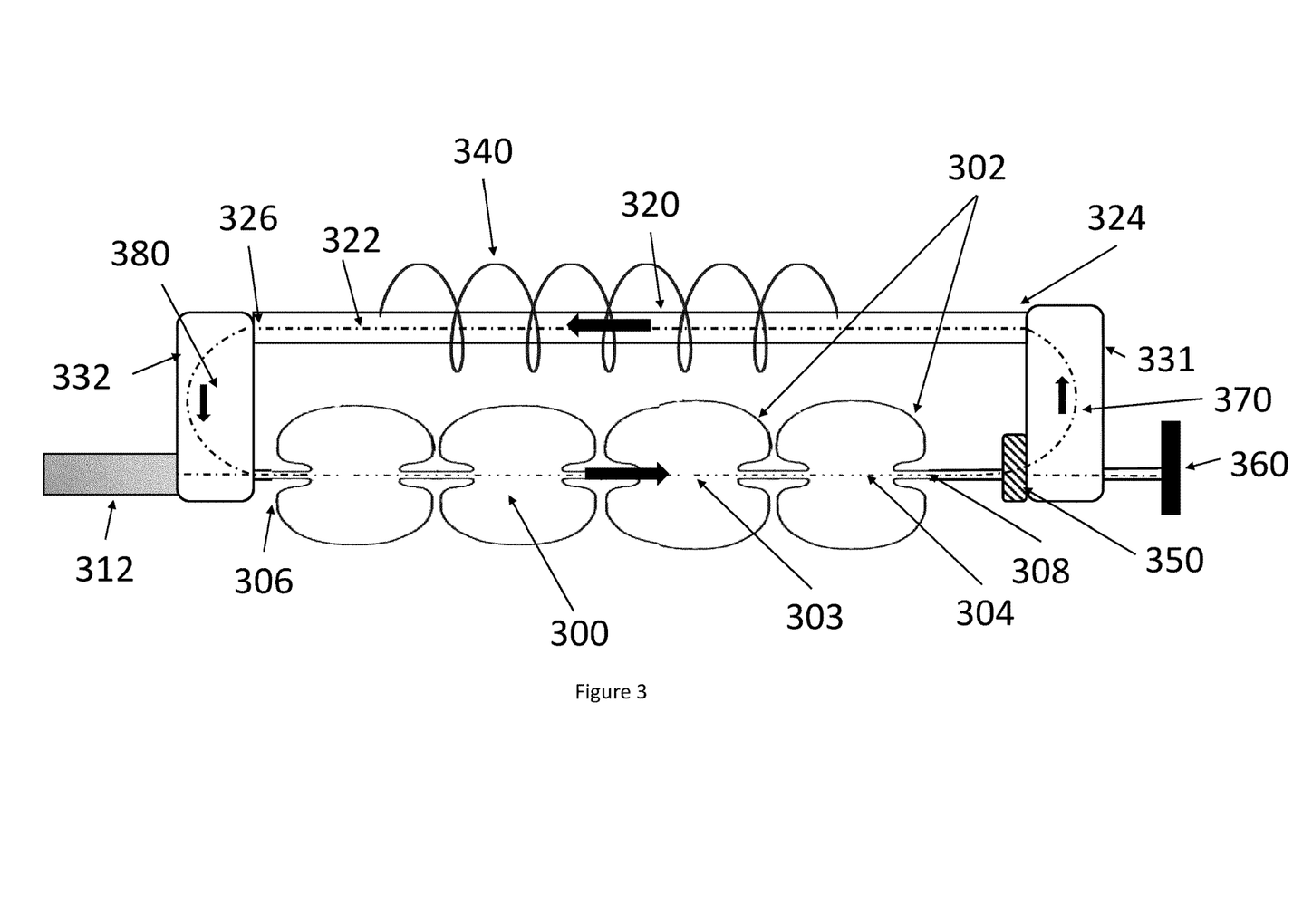
FIG. 3 illustrates a first particle accelerator according to the present disclosure.

FIG. 3 shows a first dual energy particle accelerator for use in a LINAC system. The first dual energy particle accelerator comprises a waveguide 300. The waveguide 300 is the same as the waveguide 200 shown in FIG. 2, however, additional features of the claimed invention are depicted. The waveguide 300 includes a source of electrons 312, a series of accelerating cells 302, a source of RF electromagnetic waves (not shown) and a central axis 303 which the electron beam propagates along. The waveguide 300 is configured to accelerate a beam of electrons along the central axis 303 of the acceleration cells. The waveguide 300 comprises a first end 306 and second end 308. The electrons are input into the waveguide by the source of electrons 312 (i.e. an electron gun producing an initial source of electrons). The electrons enter the waveguide 300 at the first end 306 and are then accelerated along the waveguide towards the second end 308 of the waveguide.

A diversion channel 320 is also shown in FIG. 3. The diversion channel 320 is configured to convey a beam of electrons 322. The diversion channel 320 is positioned adjacent to the waveguide 300. The central axis of the waveguide 303 and the central axis of the diversion channel 320 may be parallel to each other and separated by a separation distance. The diversion channel has a first end 324 and a second end 326. The first end 324 of the diversion channel is located adjacent to the second end 308 of the waveguide. Similarly, the second end 326 of the diversion channel 320 is located adjacent to the first end 306 of the waveguide 300.

In use, the beam of electrons 304 is removed from the second end 308 of the waveguide 300 at a first location 370 and inserted into the diversion channel 320 and redirected along the diversion channel 320 to the first end 306 of the waveguide 300 at a second location 380. This allows the recirculation of electrons in a loop, as is shown in FIG. 3. The bold arrows in FIG. 3 show the direction of travel of the electrons.

The first end 324 of the diversion channel is located as close as possible to the second end 308 of the waveguide, such that the beam of electrons 304 can be easily removed from the waveguide 300 and directed into the diversion channel 320. The second end 326 of the diversion channel 320 is located as close as possible to the first end 306 of the waveguide 300, such that the beam of electrons 322 can be easily removed from the diversion channel 320 and directed into the waveguide 300.

FIG. 3 shows first 331 and second 332 magnet arrangements. The first magnet arrangement 331 is the means by which the electrons travelling along the acceleration path can be diverted from the waveguide 300 to the diversion channel 320. The second magnet arrangement 332 is the means by which electrons travelling along the diversion channel 320 can be diverted back into the waveguide 300. Therefore, the first 331 and second 332 magnet arrangement make the recirculation of electrons possible.

Electrons are negatively charged particles and electrostatic attraction can be used to change the direction of movement of electrons when in a magnetic field. The first magnet arrangement 331 removes the beam of electrons 304 from the waveguide 300 and inserts the beam of electrons 322 into the diversion channel 320 at the first location 260. Then, the second magnet arrangement 332 removes the beam of electrons 322 from the diversion channel 320 and inserts the beam of electrons 304 back into the waveguide 300 at the second location 380. The first magnet arrangement 331 removes the beam of electrons 304 from the second end 308 of the waveguide 300 and inserts the beam 322 of electrons into the first end of the diversion channel. Then, subsequently the second magnet arrangement 332 to removes the beam of electrons 322 from the second end 326 of the diversion channel 320 and inserts the beam of electrons 308 into the first end 306 of the waveguide 300.

As previously mentioned, the beam of electrons 304 may enter the first end 306 of the waveguide from the source of electrons 312. Alternatively, the beam of electrons may be input into the waveguide 300 via the recirculation process, i.e. the beam of electrons 322 in the diversion channel 320 may enter the first end 306 of the waveguide 300 and join the beam of electrons 304 in the waveguide 300. It is possible that the particle accelerator has multiple modes: a mode in which the source of electrons 312 is the sole source of electrons input into the acceleration cells 302 and a separate mode in which the recirculated electrons from the diversion channel 320 are the sole source of electrons input into the acceleration cells. Additionally, it is also possible that electrons are input into the waveguide 300 via both the source of electrons 312 (i.e. electron gun) and via the diversion channel 320 at the same time.

The particle accelerator is configured such that beam of electrons 304 travels in a primary direction along the central axis of the acceleration cells 303 of the waveguide 300; and the electrons travel in a secondary direction along the diversion channel 320. The secondary direction may be parallel, or substantially parallel, and opposite to the primary direction, as shown by the bold arrows in FIG. 3.

The first magnet arrangement 331 is located at the first location 370 at the second end 308 of the waveguide and the second magnet arrangement 332 is located at the second location 380 at the first end 306 of the waveguide. Alternatively, the second magnet arrangement 332 is located at the intersection between the source of electrons 312 and the first end 306 of the waveguide 300. The first magnet arrangement 331 can be located at the intersection between the second end of the waveguide 308 and metal target 360. The first magnet arrangement 331 removes the beam of electrons 304 from the waveguide 300 and inserts the beam of electrons 322 into the diversion channel 320. The second magnet arrangement 332 removes the beam of electrons 322 from the diversion channel 320 and inserts the beam of electrons 304 into the waveguide 300.

The first magnet arrangement 331 is arranged such that the beam of electrons 304 enters the first magnet arrangement 331 and the direction of the electrons is changed such that the electrons are redirected into the diversion channel 320. The beam of electrons 322 in the diversion channel 320 is supplied by the first magnet arrangement 331. The beam of electrons 322 then travels along the length of the diversion channel 320. Once the beam of electrons 322 reach the end of the diversion channel 320 they encounter the second magnet arrangement 332. The electron beam enters the second magnet arrangement 332 and the direction of the electron beam is bent such that the electrons re-join the waveguide 300.

The particle accelerator may also include a solenoid 340 arrangement, as shown in FIG. 3. The solenoid 340 is positioned to surround the diversion channel 320. The purpose of the solenoid 340 is to prevent beam breakup as the beam of electrons 322 is transported through the diversion channel 320. In particular, this is important to ensure that the electrons maintain the 'bunches' formed in the waveguide 300. It is important that the electrons have enough energy when entering the diversion channel 320 to complete a full pass through the diversion channel 320 without stopping. It is therefore important to ensure that enough beam loading (i.e. the delivery of energy to the electrons) is delivered to the electrons in the waveguide 300 through the RF radiation. This energy can be maintained by the solenoid 340 to ensure that there is no beam breakup during the transmission through the diversion channel 320.

Magnet Configuration

Each magnet arrangement comprises at least one wire with an electrical current running through the wire to produce a magnetic field. The magnet arrangement is formed of magnets that are used to focus and steer the beam of electrons. The magnet arrangement is formed by electric currents running through wires to produce a magnetic field. The magnetic field is used to move the negatively charged electrons.

Figure 5A:
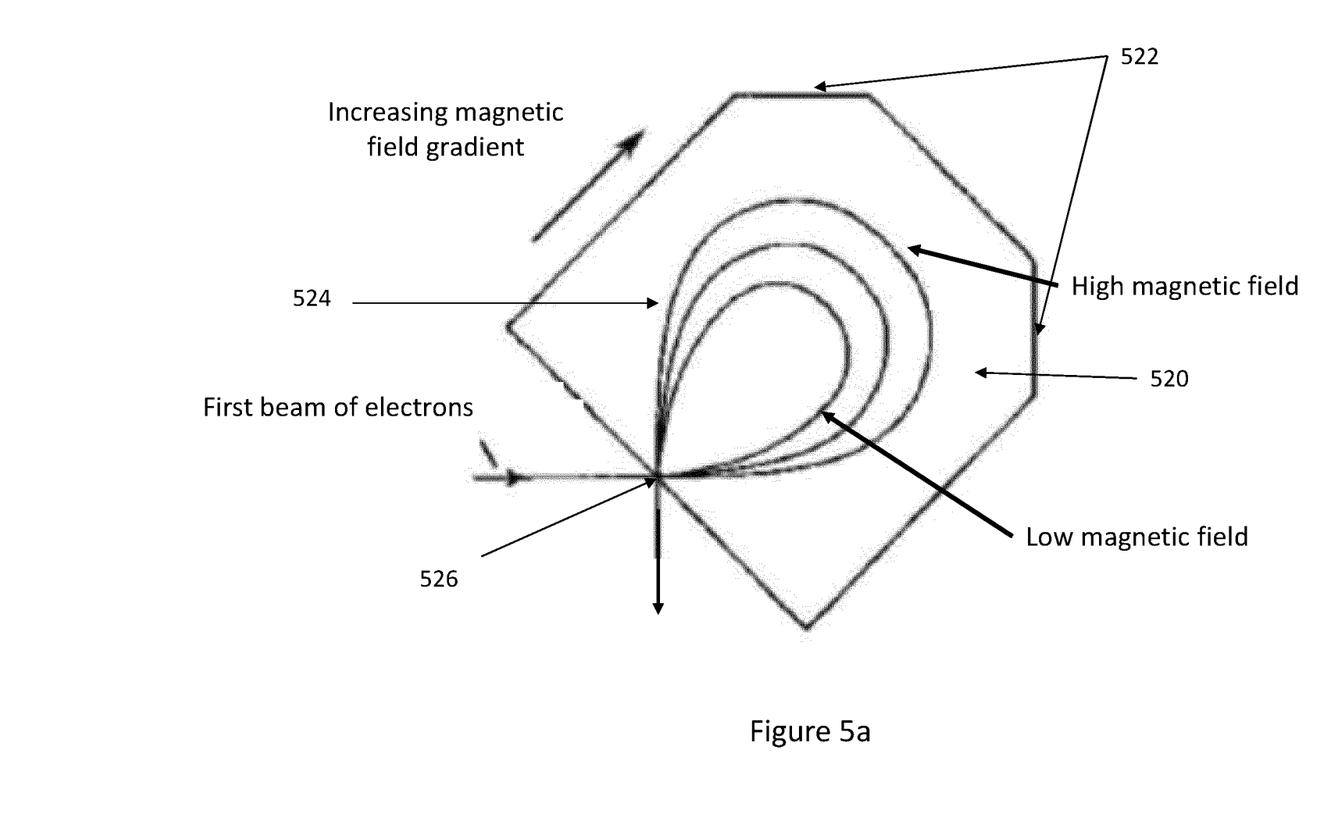
FIGS. 5a and 5b illustrate the use of an alpha magnet in the magnet arrangement.

The magnet arrangements may comprise one or more alpha magnets. An example of an alpha magnet is shown in FIG. 5a. An alpha magnet is a type of magnet that can be used to deflect a beam by 270 degrees, as shown in FIG. 5a. Alpha magnets are used in radiotherapy machines for electron beam bending to direct the beam of electrons produced by a linear accelerator towards a target 360. Alpha magnets are suitable for use in radiotherapy systems and can provide focusing for a spread of energies in a beam to a small focal spot. For example, high energy medical electron linacs are usually mounted horizontally, as shown in FIG. 1, and the emergent electron beam from the accelerating tube is deflected magnetically through 90° or 270° into a vertical plane to hit an X-ray target 360 or electron scatterer. The present invention applies alpha magnet technology to produce a dual energy LINAC.

FIG. 5a shows a square-shaped alpha magnet 520 with chamfered edges 522. The square-shaped alpha magnet 520 has a beam channel 524 carved out of it. The alpha magnet may be formed in any shape. The beam channel 524 is where the electron beam is directed, and the electron beam is bent around this channel. The electrons enter and exit the alpha magnet at the same entrance/exit point 526. The alpha magnet has a magnetic field strength that increases with increasing distance from the entrance/exit point 526. The magnetic field gradient is labelled in FIG. 5a. There is a minimum magnetic field acting on the electrons when they first enter the alpha magnet and there is a maximum magnetic field when the electrons are furthest from the entrance/exit point. Areas of high and low magnetic field are labelled on FIG. 5a. The alpha magnet is an electromagnet and the magnetic field can be adjusted by, for example, adjusting the current within the electromagnet.

The alpha magnet shown in FIG. 5a can bend a beam of electrons by 270 degrees. A single alpha magnet can be used to divert all the electrons. The alpha magnet is achromatic, meaning that electrons of different energies are focussed to the same point. This can be seen from the different electron beam paths shown in FIG. 5a. Electrons of different energies are accelerated and decelerated at different rates, however all these electrons exit the alpha magnet at the same position.

Figure 5B:
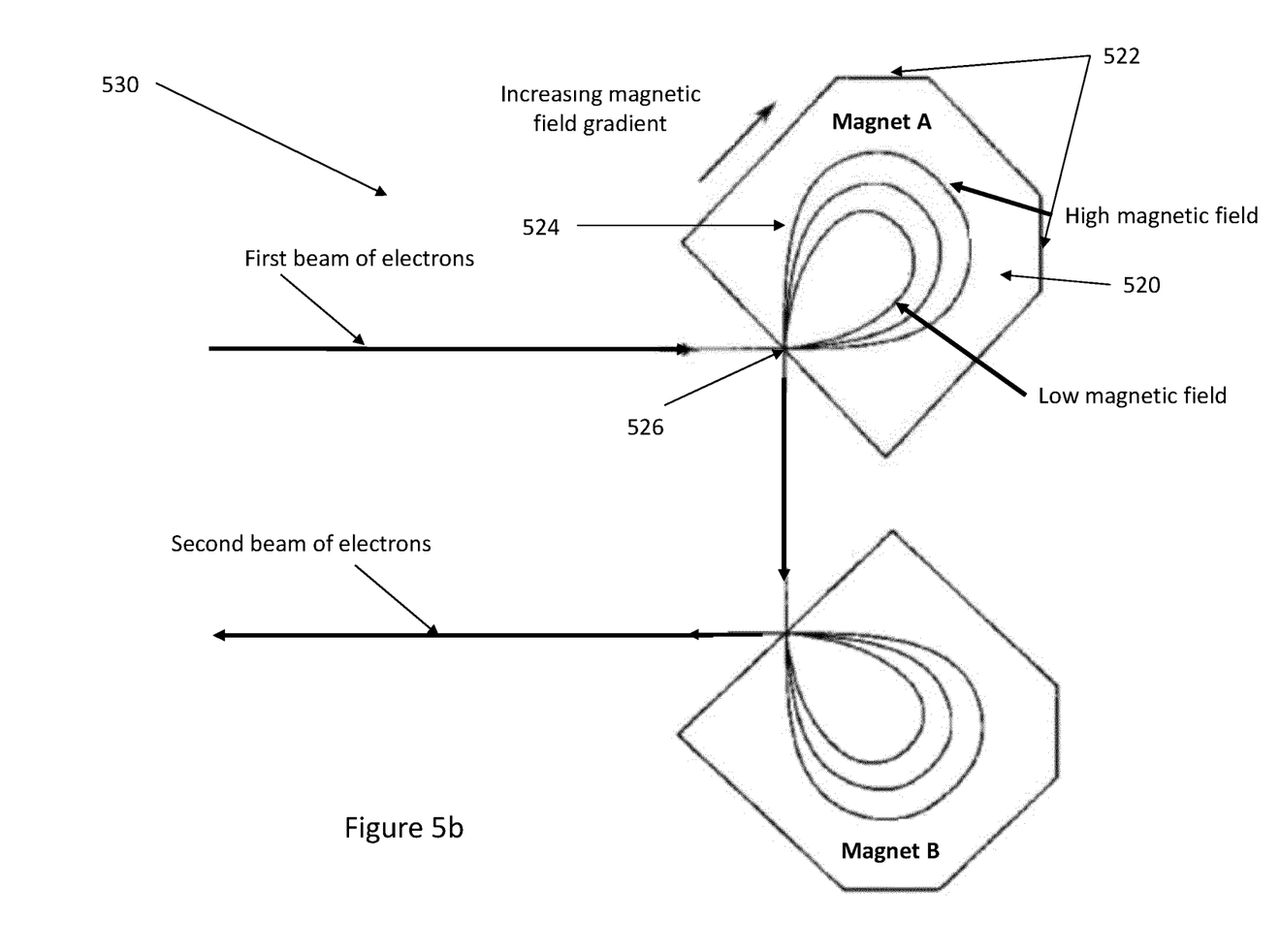

FIG. 5b shows a magnet arrangement (e.g. the first magnet arrangement or second magnet arrangement) comprising a first alpha magnet and a second alpha magnet. In the example in the figures both the first alpha magnet (magnet A) and the second alpha magnet (magnet B) are identical and are the same as the single magnet shown in FIG. 5a. The first alpha magnet (magnet A) and the second alpha magnet (magnet B) are positioned next to each other. The first alpha magnet (magnet A) is angled at 90 degrees to the second alpha magnet (magnet B). The magnet arrangement is arranged such that beam of electrons traveling towards the electron gun are, firstly, redirected by an angle of 270 degrees by the first alpha magnet, and secondly, they are redirected by an angle of 270 degrees by the second alpha magnet. As shown in FIG. 5b, this combination of alpha magnet arrangement means that the beam of electrons are overall redirected by an angle of approximately 180 degrees. This means that the beam of electrons 304 can be removed from the waveguide 300 and redirected towards the diversion channel 320.

The first magnet arrangement 331 is made up of the arrangement shown in FIG. 5b. Similarly, the second magnet arrangement 332 is also made up of the arrangement shown in FIG. 5b. Therefore, the first magnet arrangement 331 and second magnet arrangement 332 comprise two alpha magnets each. A total of four alpha magnets are used to fully circulate the electrons by 360 degrees as shown in FIG. 3. The first magnet arrangement 331 is configured to change the direction of travel of the beam of electrons, when the electrons enter the first magnet arrangement 331 they are traveling in the primary direction, then after exiting the first magnet arrangement 331 they are travelling in the secondary direction. Similarly, when the electrons enter the second magnet arrangement 332 they are traveling in the secondary direction, then after exiting the second magnet arrangement 332 they are travelling in the primary direction. The secondary direction may be parallel and opposite to the primary direction, as shown by the bold arrows in FIG. 3.

It is advantageous to use two alpha magnets in each of the first and second magnet arrangements as the magnetic field can be adjusted to alter the angle of the redirected electrons (not shown). For example, electrons can be travelling in a variety of directions when they reach the alpha magnets. It is therefore desirable to ensure that the redirected electrons are redirected by the exact angle needed to allow the electrons to join the beam of electrons. The angle of the redirected electrons can be altered by adjusting the angle between the alpha magnets or by altering the magnetic fields within the alpha magnets.

These type of magnet arrangements are applicable to a standing waveguide or a travelling waveguide. This type of magnet is advantageous because it has a very small bending radius of 2 cm meaning that very little additional space is required in the particle accelerator. The alpha magnets can require a cooling mechanism (not shown) to prevent overheating.

Off-Axis Electron Gun

Figure 4:
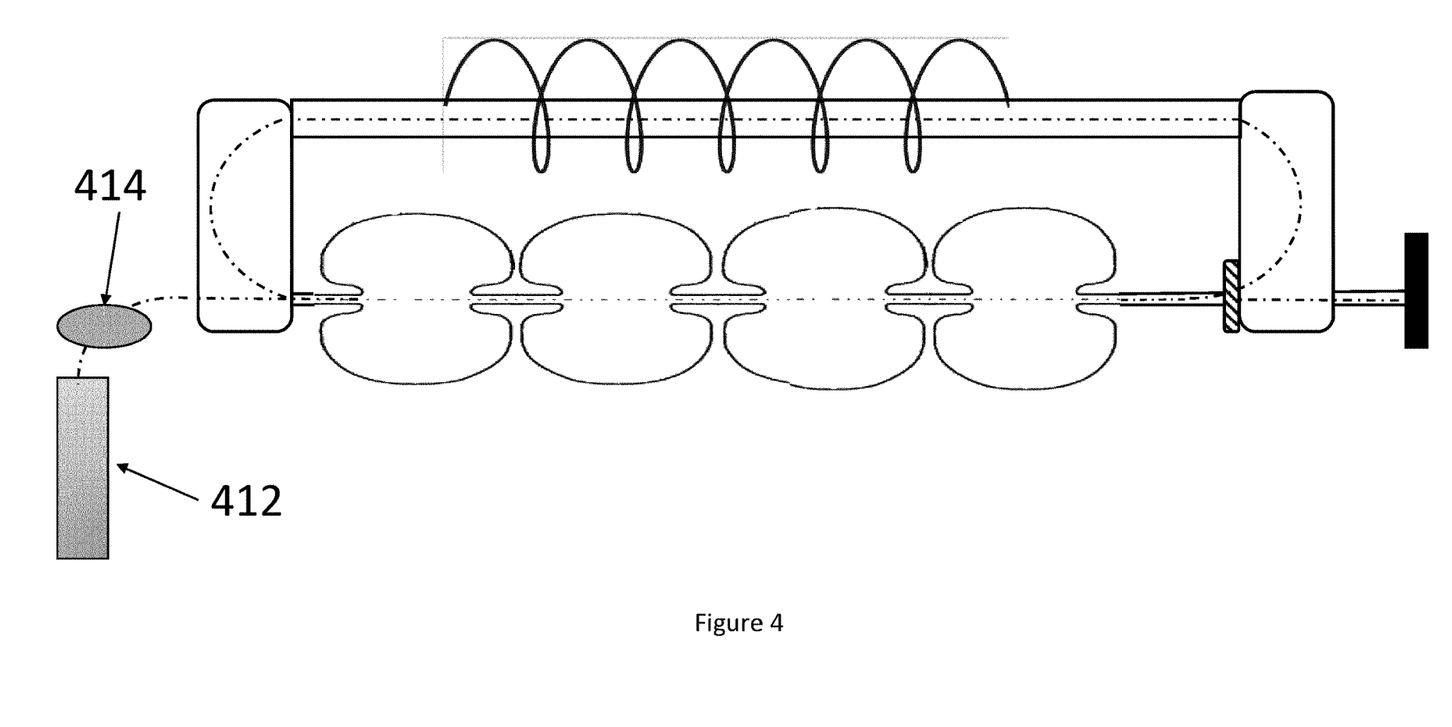
FIG. 4 illustrates the first particle accelerator according to the present disclosure including an off-axis source of electrons.

To use an alpha magnet arrangement as shown in FIGS. 5a and 5b, it would also be desirable to move the electron gun off axis as shown in FIG. 4, such that it is not located along the central axis 303 of the acceleration cells. This ensures that the magnetic field of the second magnet arrangement does not affect the electrons when they first enter the first end of the waveguide. To achieve this, the beam of electrons entering the input accelerating cell from the 'off axis' electron gun 412 will be bent by using an electron gun magnet arrangement 414. The electron gun magnet arrangement may also comprise an alpha magnet, similar to the one shown in FIG. 5a. When the electron gun is off axis, the 'backbomardment' of electrons from the waveguide back towards the electron gun causing damage is not an issue and neither is rundown law. Rundown law occurs when 'backbomarded' electrons cause an increase heat in the electron gun and a process by which unwanted electrons are exponentially produced, potentially causing significant damage to the LINAC. The magnet arrangements therefore helps to simplify some of the many issues that LINACs are faced with.

It is also possible to include more than one electron gun 312 (not shown). For example, multiple electron guns 312 could be located 'off axis' and directed into the first end 306 of the waveguide 300. This would allow the number of the electrons inserted into the waveguide 300 to be increased. It would also mean that the electron guns are not required to run at full power, thereby extending the life of the guns.

FIG. 3 also shows an electromagnetic kicker magnet 350 (otherwise known as a septum). The electromagnetic kicker magnet 350 is positioned between the second end 308 of the waveguide 300 and the first magnet arrangement 331. The first end 324 of the diversion channel 320 is positioned adjacent to the electromagnetic kicker magnet 350. The purpose of the electromagnetic kicker magnet 350 is to determine whether the beam of electrons 304 in the waveguide 300 should be output from the waveguide 300 or recirculated into the diversion channel 320. In the first instance, when the beam of electrons 308 is output from the waveguide 300, the beam of electrons is allowed to continue in a straight line along the central axis 303 of the waveguide 300. The electrons continue towards the metal target 360 and strike the metal target 360, producing x-rays for medical use. In the second instance, the electromagnetic kicker magnet is designed to recirculate the electrons by diverting them into the first magnet arrangement 331. When the electrons reach the first magnet arrangement 331, the direction of movement is adjusted, as previously explained, and the electrons are diverted into the diversion channel 320.

The electromagnetic kicker magnet 350 comprises a first state and a second state. When the electromagnetic kicker magnet 350 is set to the first state the beam of electrons 304 continues to travel along the central axis 303 of the acceleration cells towards the target 360. When the electromagnetic kicker magnet 350 is set to the second state the beam of electrons 304 is removed from the series of acceleration cells 302 and inserted into the diversion channel 320. When the electromagnetic kicker magnet 350 is set to the first state, the electrons are allowed to directly pass through the waveguide 300 and exit, this means that they are only accelerated once through the waveguide, resulting in a first energy output, for a typical waveguide systems this is approximately 6 MV. When the electromagnetic kicker magnet 350 is set to the second state, the electrons are recirculated through the diversion channel 320 and pass through the waveguide 300 twice, at this stage the electrons are then output from the waveguide 300 having passed through the waveguide 300 twice and having been through the acceleration process twice. In order to achieve this the electromagnetic kicker 350 is initially set to the second state causing the electron beam to be diverted through the diversion channel, then the electromagnetic kicker is set to the first state to allow the electrons to exit from the waveguide towards the target 360. This results in a second output energy, in a typical waveguide system this would be approximately 10 MV. The electrons do not receive exactly double the amount of energy, due to some energy lost in the bending and diversion process. In order to achieve the switch in states it is necessary that the electrons are formed in coherent 'bunches' to ensure that the electromagnetic kicker magnet 350 can select the correct setting (i.e. either the first or second state).

Similarly, it is also possible for the electrons to be circulated through the waveguide 300 and diversion channels 350 multiple times. On each pass through the waveguide 300 more energy is delivered to the electrons and a higher order of output energy can be achieved.

Shielding (not shown) can be fixed around the outside of the diversion channel 320, magnet arrangements and electromagnetic kicker magnet 350 to ensure that no electrons escape from the particle accelerator as they are recirculated through the diversion channel 320. It is desirable to prevent electrons from escaping as they can cause damage to other components of the medical device and may reduce the durability of the machine.

Method

Figure 6:
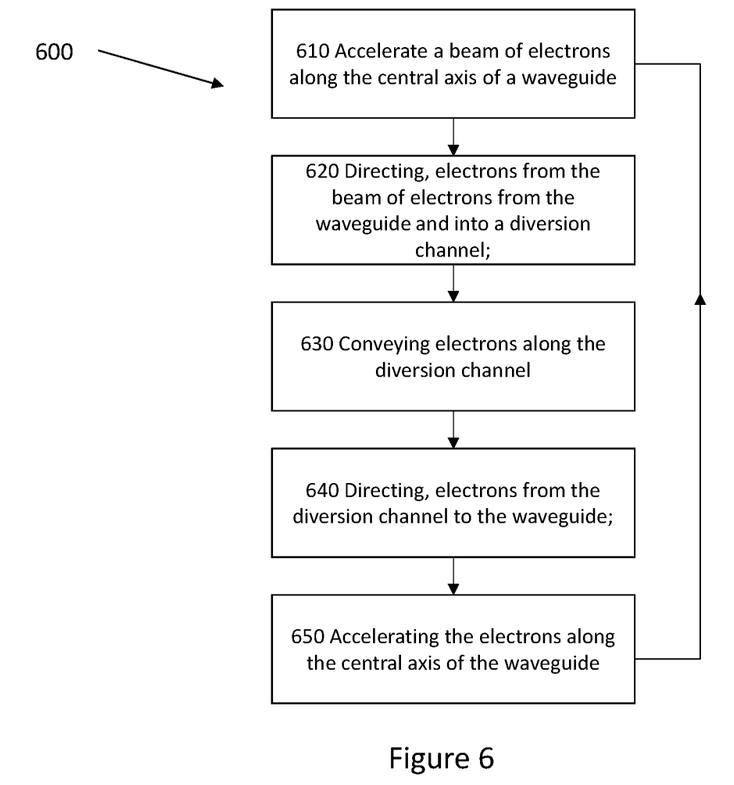
FIG. 6 illustrates a first method according to present disclosure.

FIG. 6 depicts a method 600 according to the present disclosure. At 610, a beam of electrons is accelerated along the central axis of a waveguide 300. The electrons are inserted into the waveguide 300 after being generated by a source of electrons 312.

At 620, the electrons are diverted from the beam of electrons from the waveguide into the diversion channel. This is done using a first magnet arrangement 331. The first magnet arrangement 331 removes the beam of electrons 304 from the waveguide 300 and inserts the beam of electrons 322 into the diversion channel 320.

At 630, electrons are conveyed along the diversion channel 320. A solenoid 340 is used to prevent beam breakup as the beam of electrons 322 is transported through the diversion channel 320. Therefore, diversion channel maintains the 'bunches' of electrons formed in the waveguide 300.

At 640, the electrons are diverted from the diversion channel 320 to the waveguide 300. The second magnet arrangement 332 removes the beam of electrons 322 from the diversion channel 320 and inserts the beam of electrons 304 into the waveguide 300.

The method described in FIG. 6 can be completed multiple times depending on how many times the electrons are to be recirculated through the waveguide (i.e. moving from step 650 back to step 610 after completing the method once). For each time the method is repeated the electrons receive more energy and a higher resultant electron beam is delivered by the waveguide.

Alternative Dual Energy Particle Accelerator Configuration

There is provided a second type of dual energy (mode) particle accelerator. This second type of dual energy particle accelerator is also capable of producing two different electron beams with two separate energies. In a first mode a first energy is produced by passing an electron beam through a LINAC standing waveguide or travelling waveguide. In this instance, the electron beam passes through a single acceleration channel. In a second mode a second energy is produced by passing an electron beam through two LINAC standing or travelling waveguides. In the second mode, the electron beam passes through two acceleration channels and acquires more energy. The dual energy mode particle accelerator can switch between modes to produce first and second electron beams with different energies to tailor to the requirements of the patient treatment plan.

Figure 7:
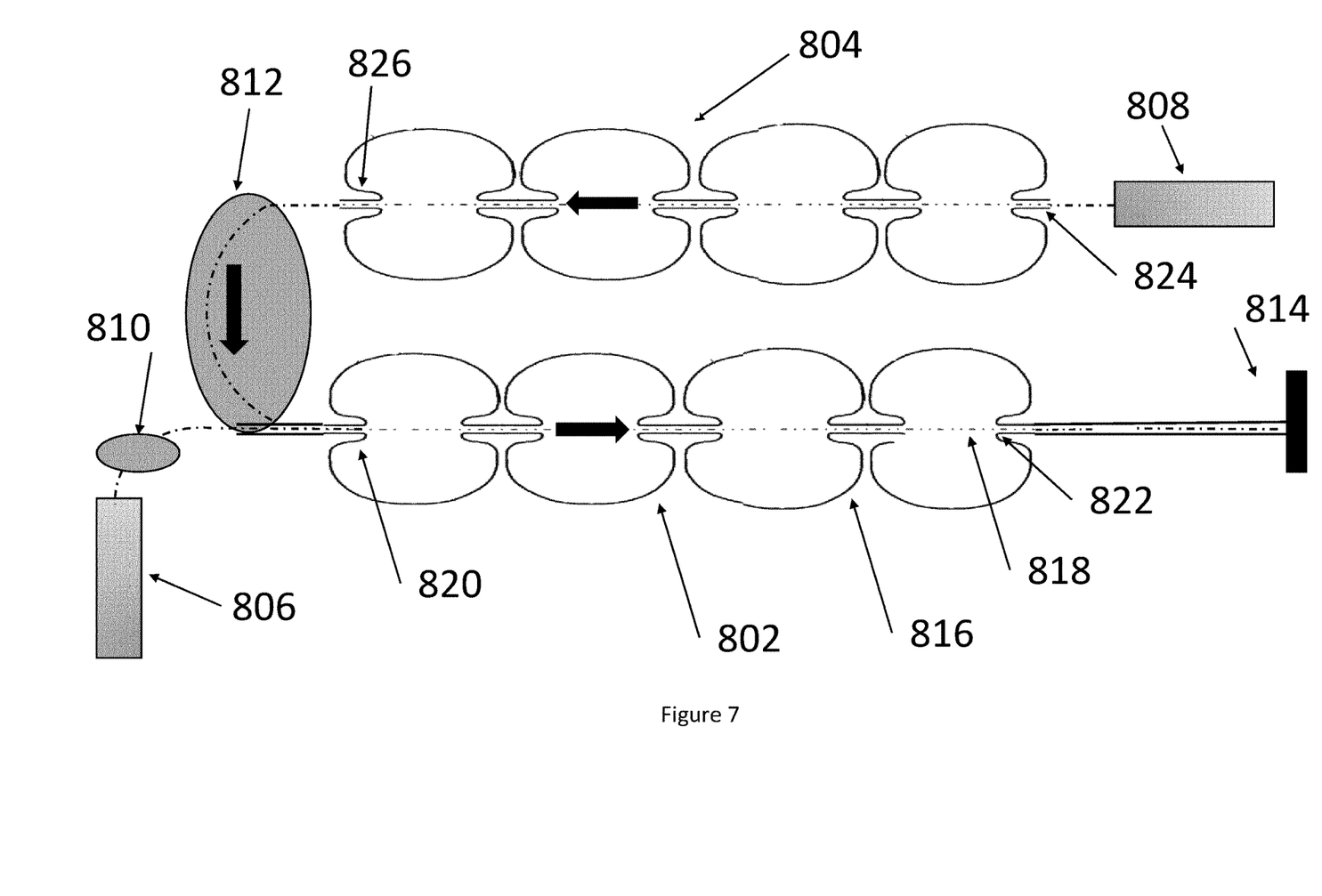
FIG. 7 illustrates a second particle accelerator according to the present disclosure.

FIG. 7 shows the second type of dual energy particle accelerator. The particle accelerator comprises a first waveguide 802 and a second waveguide 804. The first 802 and second 804 waveguides are the same as the waveguide 200 shown in FIG. 2, however, additional features are also depicted in FIG. 7. The first waveguide 802 includes a source of electrons 806 that is located 'off-axis', such that it is not located along the central axis of the acceleration cells of the waveguide. This has the same benefits as previously described for 'off-axis' sources of electrons. Additionally, the 'off-axis' electron gun allows a second magnet arrangement 812 to be used without any obstruction. To deliver a beam of electrons into the input accelerating cell electrons from the 'off axis' electron gun 806 will be bent by using an electron gun magnet arrangement 810. The electron gun magnet arrangement 810 may comprise an alpha magnet, similar to the one shown in FIG. 5a. Alternatively, the electron gun magnet arrangement could be a simple dipole magnet. The electrons are input into the waveguide by the source of electrons 806 (i.e. an electron gun producing an initial source of electrons). The electrons enter the waveguide 802 are then accelerated along the waveguide towards the opposite end of the waveguide.

The first waveguide 802 comprises a series of accelerating cells 816, a source of RF electromagnetic waves (not shown) and a central axis 818 which the electron beam propagates along. The waveguide has a first end 820 and a second end 822. The electrons are input into the first end 820 of the waveguide 802 by the source of electrons 806.

A second waveguide 804 is also shown in FIG. 7. The second waveguide 804 is identical to the first waveguide 802. The second waveguide 804 is located parallel, or substantially parallel, to the first waveguide 802, and separated by a separation distance. The particle accelerator is configured such that beam of electrons travels in a primary direction along the central axis of the acceleration cell of the first waveguide 802 and the electrons travel in a secondary direction along the central axis of the acceleration cells of the second waveguide 804. The secondary direction may be parallel, or substantially parallel, and opposite to the primary direction, as shown by the bold arrows in FIG. 7.

A second electron gun 808 inserts electrons into the second waveguide 804. The second electron gun 808 does not necessarily need to be located off axis, although in some configurations it is. The second waveguide 804 has a first end 824 and a second end 826. The second end 826 of the second waveguide 804 is located adjacent to the first end 820 of the first waveguide 802. In use, in the second mode in which the second waveguide 804 is in use, a beam of electrons travelling in the secondary direction along the central axis of the second waveguide 804 removed from the second end 826 of the second waveguide 826 and inserted into the first waveguide 802. This allows the circulation of electrons, as is shown in FIG. 7. The bold arrows in FIG. 7 show the direction of travel of the electrons.

The second end 826 of the second waveguide 804 located as close as possible to the first end 820 of the first waveguide 802, such that the beam of electrons can be easily removed from the second waveguide 804 and directed into the first waveguide 802. The second magnet arrangement 812 removes the beam of electrons from the second waveguide 804 and inserts the beam of electrons into the first waveguide 802 at the first location. The second magnet arrangement 812 is arranged such that the beam of electrons enters the second magnet arrangement 812 and the direction of the electrons is changed such that the electrons are redirected into the first waveguide 802. The second magnet arrangement 812 may comprise two alpha magnets, as shown in FIG. 5b. As shown in FIG. 5b, this combination of alpha magnet arrangement means that the beam of electrons is overall redirected by an angle of approximately 180 degrees. This means that the beam of electrons can be removed from the second waveguide 804 and redirected towards the first waveguide 802.

When the second magnet arrangement comprises two alpha magnets, the first alpha magnet is positioned to receive electrons from the second waveguide, the second alpha magnet is positioned to receive electrons from the first alpha magnet, and first alpha magnet is angled at 90 degrees to the second alpha magnet.

The second type of dual energy (mode) particle accelerator creates a dual energy by switching between two modes. In the first mode the first electron gun 806 and first waveguide 802 are used. In this first mode the electrons are delivered into the first waveguide 802 and pass through the first waveguide once and subsequently hit the target 814 (similar to the process shown in FIG. 2). This produces a beam having a first energy e.g. 6 MV. In a second mode the first electron gun 806 is not used. Instead, the second electron gun 808 and the first 802 and second 804 waveguides are both used. During the second mode electrons are first inserted into the second waveguide 804 using the second electron gun 808. The electrons are accelerated along the central axis of the second waveguide 804 and are then redirected by the second magnet arrangement 812 into the first waveguide 802. The electrons subsequently pass the whole length of the first waveguide 802, being accelerated along the central axis of the first waveguide 802, and then hit the target 814. In the second mode the electrons have passed through two waveguides, receiving more energy than a beam having accelerated in a single waveguide, therefore producing a higher order second energy beam e.g. 10 MV. The particle accelerator can be switched between the first and second modes to produce the desired energy depending on the patient's treatment plan.

Additionally, it is also possible to use the second type of dual energy particle accelerator in a third mode. In the third mode both the first 806 and second 808 electron guns are turned on. Electrons can be input into the first waveguide 802 from the first electron gun 806 and from the second magnet arrangement 812 (i.e. having already passed through the second waveguide 804). This results in an electron beam that has electrons with a combination of the two types of energies, for example, electrons of both 6 MV and 10 MV are present in the resultant beam.

Figure 8:
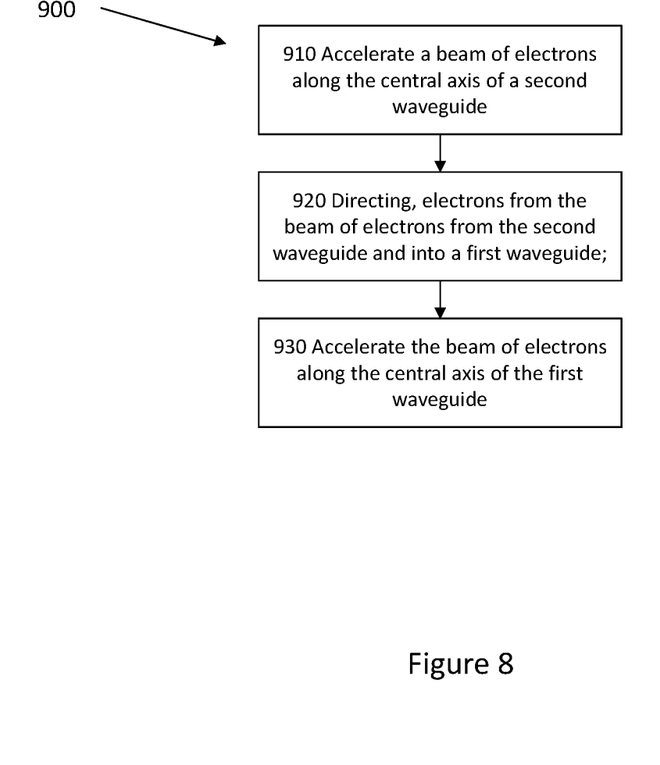
FIG. 8 illustrates a second method according to present disclosure.

FIG. 8 depicts a method 900 according to the present disclosure in relation to the second type of dual energy particle accelerator when in the second mode. At 910, a beam of electrons is accelerated along the central axis of the second waveguide 804. The electrons are inserted into the second waveguide 804 after being generated by a source of electrons 808.

At 920, the electrons are diverted from the second waveguide 804 into the first waveguide 802. This is done using the second magnet arrangement 812.

At 930, the beam of electrons is accelerated along the central axis of the first waveguide 802. A resulting beam having the second energy is produced.

Advantages of the Invention

The claimed invention produces a LINAC that has the capability of producing a beam of electrons with multiple different energies (for example, to produce energies of both 6 MV and 10 MV in a single machine). These multiple energies are useful for varying the length of time of exposure to radiation and for modifying individual patient treatment plans depending on the patient's needs. For example, in some circumstances it is useful to produce a lower energy beam (e.g. 6 MV) when a lower dosage rate is desirable, as higher dosage may compromise patient health. However, in other circumstances is beneficial to produce a higher energy (e.g. 10 MV) and therefore increase the dosage rate to speed up treatment times. Evidently, the medical profession can benefit from quicker treatment times and the ability to treat more patients. It is particularly beneficial to produce both energies within the same machine as it prevents having to use separate machines for different energy requirements.

It is also desirable to be able to produce an electron beam that contains two types of energies at the same time (e.g. both 6 MV and 10 MV in the same beam). This has the added advantage of speeding up the treatment across the volume of a tumour by treating both the front and back of the tumour with different energies. This reduces the time spent adjusting filters used to deliver the correct energy dosage.

The described apparatus can be applied to either a standing waveguide system or traveling waveguide system, but it is necessary to ensure that the beam is well focused and there is a surplus of energy for beam loading to ensure that there is enough energy for the electrons to complete a full transmission along the length of the diversion channel.

The claimed invention can be applied as a factory standard, i.e. fitted to the waveguide machine when it is initially installed. Alternatively, the components parts required for the recirculation of electrons can be added to the device at a later date. For example, the diversion channel and magnet arrangements can be added to an already working LINAC system.

Features of the above aspects can be combined in any suitable manner. It will be understood that the above description is of specific embodiments by way of aspect only and that many modifications and alterations will be within the skilled person's reach and are intended to be covered by the scope of the appendant claims.

The invention claimed is:

1. A particle accelerator comprising:
 a waveguide configured to accelerate a beam of electrons along an acceleration path;
 a diversion channel configured to convey the beam of electrons along a diversion path, wherein the diversion channel comprises a solenoid arrangement;
 a first magnet arrangement configured to, at a first location, direct electrons from the acceleration path to the diversion path;
 a second magnet arrangement configured to, at a second location, direct electrons from the diversion path to the acceleration path; and
 an electromagnetic kicker magnet, wherein the electromagnetic kicker magnet is positioned between a second end of the waveguide and the first magnet arrangement, and wherein the electromagnetic kicker magnet comprises:
  a first state; and
  a second state, wherein when the electromagnetic kicker magnet is set to the first state, the beam of electrons continues to travel along a central axis of the waveguide towards a target, wherein when the electromagnetic kicker magnet is set to the second state, the beam of electrons is removed from the waveguide and inserted into the diversion channel, and wherein a first end of the diversion channel is positioned adjacent to the electromagnetic kicker magnet.

2. The particle accelerator of claim 1, wherein the waveguide comprises a first end and second end, wherein the diversion channel comprises a first end and a second end, wherein the first magnet arrangement is configured to remove the beam of electrons from the second end of the waveguide and insert the beam of electrons into the first end of the diversion channel at the first location, and wherein the second magnet arrangement is configured to remove the beam of electrons from the second end of the diversion channel and insert the beam of electrons into the first end of the waveguide at the second location.

3. The particle accelerator of claim 1, further comprising:
 a source of electrons configured to input electrons into a first end of the waveguide and wherein the waveguide is configured to direct the electrons along the acceleration path towards a second end of the waveguide.

4. The particle accelerator of claim 3, wherein the second magnet arrangement is located at an intersection between the source of electrons and the first end of the waveguide.

5. The particle accelerator of claim 2, further comprising:
 a target configured to produce X-rays when hit by the beam of electrons, wherein the target is proximate the second end of the waveguide.

6. The particle accelerator of claim 5, wherein the first magnet arrangement is located at an intersection between the second end of the waveguide and the target.

7. The particle accelerator of claim 1, wherein the waveguide is configured such that beam of electrons travels in a primary direction along the central axis of the waveguide, wherein the diversion channel is configured such that the beam of electrons travels in a secondary direction along the diversion channel, wherein the secondary direction is parallel and opposite to the primary direction, and wherein the diversion channel comprises a second waveguide configured to accelerate a beam of electrons along a second acceleration path.

8. The particle accelerator of claim 7, comprising:
a source of electrons which is positioned at a location offset from the central axis of the waveguide.

9. The particle accelerator of claim 1, wherein the first magnet arrangement and second magnet arrangement each comprise at least one alpha magnet, the alpha magnet comprising:
an entrance point configured to receive electrons travelling in a first direction; and
a magnetic field of increasing strength in a direction away from the entrance point, such that received electrons travel along a beam path and exit the magnet at the entrance point travelling in a second direction.

10. The particle accelerator of claim 9, wherein the second direction is angled at 270 degrees to the first direction.

11. The particle accelerator of claim 9, wherein the first magnet arrangement and second magnet arrangement each comprise:
a first alpha magnet and a second alpha magnet, wherein the first alpha magnet is positioned to receive electrons from the waveguide, wherein the second alpha magnet is positioned to receive electrons from the first alpha magnet, and wherein the first alpha magnet is angled at 90 degrees to the second alpha magnet.

12. The particle accelerator of claim 1, further comprising:
a source of electromagnetic radiation configured to supply electromagnetic radiation to the waveguide to accelerate the beam of electrons.

\* \* \* \* \*